(12) United States Patent
Green

(10) Patent No.: US 10,041,907 B2
(45) Date of Patent: Aug. 7, 2018

(54) ACCURATE MOBILITY CHROMATOGRAMS

(71) Applicant: Micromass UK Limited, Wilmslow (GB)

(72) Inventor: Martin Raymond Green, Bowdon (GB)

(73) Assignee: MICROMASS UK LIMITED, Wilmslow (GB)

( * ) Notice: Subject to any disclaimer, the term of this patent is extended or adjusted under 35 U.S.C. 154(b) by 0 days.

(21) Appl. No.: 15/514,029

(22) PCT Filed: Sep. 25, 2015

(86) PCT No.: PCT/GB2015/000273
§ 371 (c)(1),
(2) Date: Mar. 24, 2017

(87) PCT Pub. No.: WO2016/046513
PCT Pub. Date: Mar. 31, 2016

(65) Prior Publication Data
US 2017/0276645 A1    Sep. 28, 2017

(30) Foreign Application Priority Data

Sep. 26, 2014  (EP) .................................. 14186565
Sep. 26, 2014  (GB) .................................. 1417016.1

(51) Int. Cl.
*H01J 49/06* (2006.01)
*H01J 49/40* (2006.01)
(Continued)

(52) U.S. Cl.
CPC ....... *G01N 27/622* (2013.01); *G01N 30/7233* (2013.01); *G01N 30/8631* (2013.01);
(Continued)

(58) Field of Classification Search
CPC ...... H01J 49/004; H01J 49/0036; H01J 49/40; H01J 49/0027; H01J 49/0031; H01J 49/04;
(Continued)

(56) References Cited

U.S. PATENT DOCUMENTS

| | | | |
|---|---|---|---|
| 7,157,698 B2 * | 1/2007 | Makarov ............... | H01J 49/004 250/281 |
| 8,030,089 B2 * | 10/2011 | Geromanos .......... | C12Q 1/6872 436/173 |

(Continued)

FOREIGN PATENT DOCUMENTS

| | | |
|---|---|---|
| CA | 2091279 | 3/1993 |
| WO | 2009/071241 | 6/2009 |

*Primary Examiner* — David A Vanore
(74) *Attorney, Agent, or Firm* — Womble Bond Dickinson (US) LLP; Deborah M. Vernon; Heath T. Misley

(57) ABSTRACT

A method of mass spectrometry is disclosed comprising: a) separating first ions or components of an analyte sample according to a physicochemical property other than ion mobility; b) separating said first ions or second ions formed from said components according to ion mobility; c) detecting the intensities of said first ions, or detecting the intensities of second ions formed from said components, or detecting the intensities of ions derived from said first or second ions; wherein the intensity of the ions detected at any given time is recorded together with an associated value of said physicochemical property and an associated value of said ion mobility so as to obtain spectral data; d) examining the intensities of the spectral data as a function of said ion mobility so as to detect an intensity peak in said spectral data, determining a discrete value of ion mobility for said peak, and defining a window of values of ion mobility that encompasses said discrete value; and e) filtering said spectral data so as to include only spectral data that has been (Continued)

associated with values of ion mobility that are within said window of ion mobility values.

18 Claims, 4 Drawing Sheets

(51) Int. Cl.
| | |
|---|---|
| *G01N 27/62* | (2006.01) |
| *G01N 30/72* | (2006.01) |
| *G01N 30/86* | (2006.01) |
| *H01J 49/00* | (2006.01) |
| *H01J 49/42* | (2006.01) |

(52) U.S. Cl.
CPC ......... *H01J 49/004* (2013.01); *H01J 49/0036* (2013.01); *H01J 49/4215* (2013.01)

(58) Field of Classification Search
CPC ........ H01J 49/061; H01J 49/063; H01J 49/26; H01J 49/423; H01J 49/00; H01J 49/0018; H01J 49/0022; H01J 49/0045; H01J 49/02; H01J 49/06; H01J 49/168; G01N 27/624; G01N 27/622; G01N 30/72; G01N 30/7206; G01N 30/7233; G01N 30/8634; G01N 33/6842; G01N 33/6848; G01N 33/6851
USPC ........ 250/281, 282, 286, 287, 288, 290, 293
See application file for complete search history.

(56) References Cited

U.S. PATENT DOCUMENTS

| | | | |
|---|---|---|---|
| 8,581,178 B2* | 11/2013 | Miller | G01N 27/624 |
| | | | 250/282 |
| 8,653,446 B1* | 2/2014 | Mordehai | G01N 27/622 |
| | | | 250/281 |
| 8,755,172 B1 | 7/2014 | Gorenstein et al. | |
| 9,576,777 B2* | 2/2017 | Giles | H01J 49/004 |
| 9,683,963 B2* | 6/2017 | Verenchikov | G01N 27/622 |
| 9,779,929 B2* | 10/2017 | Goshawk | H01J 49/40 |
| 9,791,424 B2* | 10/2017 | Tate | G01N 30/8634 |
| 9,818,590 B2* | 11/2017 | Cox | H01J 49/04 |
| 2001/0030285 A1* | 10/2001 | Miller | G01N 27/624 |
| | | | 250/288 |
| 2009/0189064 A1* | 7/2009 | Miller | G01N 27/624 |
| | | | 250/282 |
| 2009/0294645 A1* | 12/2009 | Gorenstein | G06F 19/703 |
| | | | 250/282 |
| 2010/0084550 A1 | 4/2010 | Lopez-Avila et al. | |
| 2013/0080073 A1 | 3/2013 | de Corral | |
| 2013/0299688 A1* | 11/2013 | Balogh | H01J 49/168 |
| | | | 250/282 |
| 2014/0005954 A1* | 1/2014 | Richardson | H01J 49/0036 |
| | | | 702/23 |
| 2015/0233866 A1* | 8/2015 | Verenchikov | G01N 27/622 |
| | | | 250/282 |
| 2016/0025692 A1* | 1/2016 | Satake | G01N 27/624 |
| | | | 73/61.55 |
| 2016/0086783 A1* | 3/2016 | Cox | H01J 49/0027 |
| | | | 250/282 |
| 2016/0172171 A1* | 6/2016 | Wang | H01J 49/0036 |
| | | | 702/196 |

* cited by examiner

ACCURATE MOBILITY CHROMATOGRAMS

CROSS-REFERENCE TO RELATED APPLICATIONS

This application represents the U.S. National Phase of International Application number PCT/GB2015/000273 entitled "Accurate Mobility Chromatograms" filed 25 Sep. 2015, which claims priority from and the benefit of United Kingdom patent application No. 1417016.1 filed on 26 Sep. 2014 and European patent application No. 14186565.9 filed on 26 Sep. 2014. The entire contents of these applications are incorporated herein by reference.

FIELD OF THE INVENTION

The present invention relates generally to mass spectrometers.

BACKGROUND

It is known to perform the targeted analysis of analyte components using either single or tandem quadrupole mass filters. During single ion recording (SIR) analysis, the mass filter(s) is set to only transmit ions having a mass to charge ratio value that corresponds to that of the known target ion. These transmitted ions are then detected. In multiple reaction monitoring (MRM), a first quadrupole mass filter Q1 is provided that is set to only transmit parent ions having a mass to charge ratio value that corresponds to that of the known target ion. The transmitted parent ions are then fragmented and the resulting fragment ions are transmitted through a second quadrupole mass filter Q2. The second quadrupole mass filter Q2 is set to only transmit fragment ions having a mass to charge ratio value that corresponds to that of a desired product ion. These transmitted fragment ions are then detected.

The analyte ions may be separated by chromatography prior to being analysed by the mass filters. Prior to analysis, it is known to determine the chromatographic elution or retention time for each target analyte using pure standards or standards prepared in a representative matrix. Once the retention time window in which each target analyte elutes is determined, the mass filter or filters are programmed to transmit these values at the appropriate time after the start of the chromatographic separation. Standards of different concentrations are used to produce quantification calibration curves relating the signal intensity detected to the amount of analyte introduced.

In normal operation the ion current at the detector is integrated for a period of time (i.e. the dwell time) for each mass filter setting. At each time period a single time-intensity (TI) point is recorded. For a given target species, a plot or chromatogram is produced of ion current detected as a function of chromatographic retention time. Chromatographic peaks within the retention time window for the target analyte may be integrated to perform quantification of the target analyte.

It is desired to provide an improved method of mass spectrometry and an improved mass spectrometer.

SUMMARY

From a first aspect the present invention provides a method of mass spectrometry comprising:

a) separating first ions or components of an analyte sample according to a physicochemical property other than ion mobility;

b) separating said first ions or second ions formed from said components according to ion mobility;

c) detecting the intensities of said first ions, or detecting the intensities of second ions formed from said components, or detecting the intensities of ions derived from said first or second ions; wherein the intensity of the ions detected at any given time is recorded together with an associated value of said physicochemical property and an associated value of said ion mobility so as to obtain spectral data;

d) examining the intensities of the spectral data as a function of said ion mobility so as to detect an intensity peak in said spectral data, determining a discrete value of ion mobility for said peak, and defining a window of values of ion mobility that encompasses said discrete value; and e) filtering said spectral data so as to include only spectral data that has been associated with values of ion mobility that are within said window of ion mobility values.

According to the present invention, the spectral data is filtered to include only data that is associated with values of ion mobility that are within a specific window of ion mobilities. This enables data to be removed that may otherwise obscure or interfere with the intensity peak(s) when the ion signal is displayed as a function of said physicochemical property.

Also, as the present invention defines an ion mobility window about a discrete value, it is able to define an ion mobility window that is narrower than the width of the intensity peak, thus excluding spectral data gathered from interference ions that have ion mobilities that partially overlap with the analyte ion giving rise to said intensity peak.

WO 2013/140132 discloses performing a multi-dimensional survey scan of precursor ions that involves separating the ions in an ion mobility separation (IMS) device and scanning a downstream mass filter so as to produce the precursor ion spectrum of FIG. 3. This enables the precursor ions present in the sample to be identified. Multiple precursor ions of interest may then be selected for fragmentation during a single acquisition, by controlling the ions transmitted by the mass filter as a function of drift time through the IMS device such that only the precursor ions of interest are transmitted, as shown in FIG. 4. The precursor ions of interest may then be fragmented, as shown in FIG. 5. The method disclosed in WO'132 increases the duty cycle compared to previous techniques which only select a single precursor ion during each acquisition.

However, although ions may be detected as a function of ion mobility and mass to charge ratio in the precursor ion survey scan of WO'132, this method does not disclose recording the intensities of the ions (together with an associated value of ion mobility and an associated value of a physicochemical property other than ion mobility). Moreover, WO'132 neither discloses determining a discrete value of an ion peak in an ion mobility spectrum, nor defining an ion mobility window that encompasses such a discrete value. Consequently, WO'132 also does not disclose filtering the spectral data to only include spectral data associated with ion mobility values within the window of ion mobility values.

In contrast to the method described in the present application, WO'132 selectively transmits each precursor ion of interest based on the start and end drift-times that the precursor ion of interest was detected in the survey scan (FIGS. 3 and 4); rather than examining the intensities of the ion mobility spectrum, determining a discrete value of an ion mobility peak, and defining a window about that discrete value. Accordingly, the technique of WO'132 is unable to define an ion mobility window that is narrower than the ion mobility peak, e.g. in order to exclude interference ions having ion mobilities that partially overlap with the analyte ion.

The technique of WO'132 would not be modified to select a window about a discrete ion mobility value, or to filter spectral data using such a window, because in WO'132 it is desired to transmit and detect all of the ions between the start and end drift-times for a precursor ion of interest.

CA 2091279 discloses a method comprising separating ions by gas chromatography (GC) and repeatedly analysing the ions in an IMS device as they elute from the GC device. A data set comprising retention time and ion mobility data is then generated, as shown in FIG. 5. A chromatograph is then reconstructed from the data. CA'279 also discloses a 'selective mode' in which undesired peaks may be removed from the chromatogram to be reconstructed. It seems that in this mode the operator reviews a previously processed chromatogram and selects retention times of components to be excluded from the chromatogram to be reconstructed. However, the 'selective mode' does not disclose determining a discrete value of ion mobility of an ion peak (e.g. analyte peak) and then filtering the spectral data so as to only include data associated with ion mobilities that fall within an ion mobility window around the discrete value, as is taught in the present application. As such, the technique of CA'279 requires the reconstruction of the chromatogram prior to any selecting and filtering the data. Also, each component to be filtered out must selected in the 'selective mode', as opposed to simply selecting the component/data to retain as in the present disclosure.

CA'279 also describes a mode wherein a drift time window is selected so as to only include analyte peaks and exclude interfering peaks. However, this mode does not identify a discrete ion mobility value and then define an ion mobility window encompassing the discrete value. Accordingly, the technique of CA'279 is unable to define an ion mobility window that is narrower than the ion mobility peak, e.g. in order to exclude interference ions having ion mobilities that partially overlap with the analyte ion.

According to the present invention, said step of detecting the intensities may comprise detecting multiple different non-zero values of intensity.

The intensity peak may be formed from multiple different non-zero values of intensity.

The method may comprise displaying the filtered data, e.g. as a spectrum of ion intensity as a function of said physicochemical property.

The method may comprise examining the intensities of the filtered spectral data as a function of said physicochemical property so as to detect an intensity peak in said filtered spectral data, and optionally identifying the presence or quantity of a compound in the sample being analysed from the intensity peak of the filtered spectral data.

The step of filtering said spectral data may result in only a single intensity peak as a function of said physicochemical property.

The method may be a method of targeted mass spectrometry for analysing a target compound, or the method may be a method of screening a sample for a target compound; wherein the intensity peak detected in step d) and/or the intensity peak in said filtered spectral data is the intensity peak for an ion of said target compound.

The value of ion mobility for the ion of said target compound may be experimentally determined or known prior to performing the method, and said discrete value for said peak may be calibrated using the experimentally determined or known value. The window may therefore be centred on the experimentally predetermined or known ion mobility value of the ion of the target compound.

The method may comprise mass filtering the ions so as to transmit only ions of a single mass to charge ratio or a range of mass to charge ratios to a detector that performs said step of detecting, wherein said single mass to charge ratio or range of mass to charge ratios includes the mass to charge ratio of said ion of said target compound.

One or more mass filters are used to perform said mass filtering. One or more of said filters may be a quadrupole mass filter. The method may therefore be a method of single or tandem mass spectrometry.

Each of the one or more mass filters may be maintained so as to only transmit a fixed mass to charge ratio or a fixed range of mass to charge ratios, and the mass to charge ratio(s) transmitted by the mass filter may not be scanned with time.

Alternatively, the mass filter may be controlled such that a plurality of different single mass to charge ratios or different ranges of mass to charge ratios are transmitted during a plurality of different times intervals, and the method may be repeated during each of said plurality of different time intervals.

A chromatographic separation device may be used to separate the ions according to the physicochemical property.

Said physicochemical property may be the elution time from a separation device, optionally from a chromatographic separation device. For example, the separation device may be a liquid chromatography column and the physicochemical property may be the retention time in the column. However, the separation device may be a device other than a liquid chromatography column.

The ions are separated according to ion mobility by an ion mobility separator. More specifically, the ions may be separated according to their mobility through a gas in the ion mobility separator. The ions may be pulsed into the ion mobility separator. Substantially all ions that enter the ion mobility separator may also exit the separator and may be substantially not filtered by the separator.

The method may comprise fragmenting, reacting or activating said first ions of step a) or said second ions of step b) so as to form said ions derived from said first or second ions in step c).

The method may comprise mass filtering said first ions or said second ions so that only ions of a single mass to charge ratio or a predetermined range of mass to charge ratios are subjected to said fragmenting, reacting or activating; and/or mass filtering said ions derived from said first or second ions so that only ions of a single mass to charge ratio or a predetermined range of mass to charge ratios are detected.

One or more mass filters are used to perform said mass filtering. One or more of said filters may be a quadrupole mass filter. The method may therefore be a method of single or tandem mass spectrometry.

Each of the one or more mass filters may be maintained so as to only transmit a fixed mass to charge ratio or a fixed range of mass to charge ratios, and the mass to charge ratio(s) transmitted by the mass filter may not be scanned with time.

The associated value of said physicochemical property for the ions detected at any given time in step c) may be based on the time at which said the ions are detected; and/or the associated value of said ion mobility for the ions detected at any given time in step c) may be based on the time at which the ions are detected.

The method described above may comprise the step of separating the first ions or separating the components of the analyte sample according to said physicochemical property; and then separating said first ions or second ions according to said ion mobility; and then fragmenting, reacting or activating the first or second ions so as to form said ions derived from said first or second ions; and then detecting the intensities of said ions derived from said first or second ions; wherein the intensity of the ions detected at any given time is recorded together with an associated value of said physicochemical property and an associated value of said ion mobility so as to obtain said spectral data; wherein the value of said physicochemical property that is associated with the ions detected at any given time is determined based on the time that the ions are detected; and wherein the value of the ion mobility that is associated with the ions detected at any given time is determined based on the time that the ions are detected.

Said physicochemical property may be the retention time in a separation device, and the value of said physicochemical property that is associated with the ions detected at any given time may be the retention time of the ions in said first ions from which said detected ions are derived, or may be the retention time of the component in said components of an analyte sample from which said detected ions are derived. Alternatively, or additionally, the value of said ion mobility that is associated with the ions detected at any given time may be the ion mobility of the ions in said first ions from which said detected ions are derived.

The discrete value determined in step d) may be obtained by determining a centroid of the intensity peak in step d).

Said window of values for said ion mobility may be narrower than the range of ion mobility values that the peak in step d) extends over.

The intensities of the spectral data as a function of said ion mobility may include a plurality of intensity peaks, each peak spanning over a different range of ion mobility values, wherein said window of values is determined for one of said peaks, and wherein the width of said window is selected to be narrow enough so as to exclude at least some of the values of ion mobility that are in one or more other peaks.

Only a single peak of the plurality of peaks may relate to the ion of the target compound. Alternatively, the ion of the target compound may have more than one charge state and hence may provide more than one peak. In such cases, one of said windows may be provided for each peak that is related to the ion of the target compound, and the spectral data may be filtered to include only spectral data that has been associated with values of ion mobility that are within said windows of ion mobility values. This technique with multiple windows is particularly useful when analysing targets from peptides.

Said window may be centred about said discrete value of ion mobility. When more than one window is used, each window may be centred about a discrete value of ion mobility.

The method may comprise determining a discrete value of ion mobility for each of said one or more other peaks, wherein said window is defined so as to exclude the discrete value(s) of said one or more other peaks.

At least some of the plurality of intensity peaks may span over ranges of values for said ion mobility that overlap with each other.

The intensities of the (unfiltered) spectral data as a function of said physicochemical property may include a plurality of intensity peaks, each peak spanning over a different range of values for said physicochemical property, wherein at least some of the plurality of intensity peaks span over ranges of values for said physicochemical property that overlap with each other.

The step of separating said first ions or separating said components of said analyte sample according to said physicochemical property may be performed over a first time scale; and said step of separating said first ions or second ions according to said ion mobility may be performed repeatedly during said first time scale. The ion mobility separation may therefore be nested within the separation according to the physicochemical property.

According to a second aspect of the present invention, there is provided a method of mass spectrometry for analysing a target compound or for screening for a target compound, said method comprising:

a) separating first ions or components of an analyte sample by retention time in a chromatographic separation device;

b) separating said first ions or second ions formed from said components according to ion mobility in an ion mobility separator;

c) mass filtering said first ions, or mass filtering second ions formed from said components, or mass filtering ions derived from said first or second ions so as to transmit to a detector only ions having a mass to charge ratio corresponding to that of an ion of said target compound;

d) detecting the intensities of the ions transmitted to the detector; wherein the intensity of the ions detected at any given time is recorded together with an associated value of retention time in said chromatographic separation device and an associated value of said ion mobility so as to obtain spectral data;

e) examining the intensities of the spectral data as a function of said ion mobility so as to detect an intensity peak for said ion of said target compound in said spectral data, determining a discrete value of ion mobility for said peak, and defining a window of values of ion mobility that encompasses said discrete value, wherein said window of values is narrower than the range of ion mobility values that said peak extends over; and f) filtering said spectral data so as to include only spectral data that has been associated with values of ion mobility that are within said window of ion mobility values.

It will be appreciated that the second aspect of the present invention is an embodiment of the first aspect of the present invention. The method of the second aspect may therefore comprise any one, or any combination of any two or more, of the optional features described in relation to the first aspect of the present invention.

The present invention also provides a mass spectrometer arranged and configured to perform any of the methods described herein.

Accordingly, the first aspect of the present invention provides a mass spectrometer comprising:

a) a separator for separating first ions or components of an analyte sample according to a physicochemical property other than ion mobility;

b) an ion mobility separator for separating said first ions or second ions formed from said components according to ion mobility;

c) a detector for detecting the intensities of said first ions, or detecting the intensities of second ions formed from said components, or detecting the intensities of ions derived from said first or second ions; wherein the spectrometer is configured such that the intensity of the ions detected at any given time is recorded together with an associated value of said physicochemical property and an associated value of said ion mobility so as to obtain spectral data; and d) a processor for examining the intensities of the spectral data as a function of said ion mobility so as to detect an intensity peak in said spectral data, determine a discrete value of said ion mobility for said peak, and set a window of values for said ion mobility that encompasses said discrete value; and for filtering said spectral data so as to include only spectral data that has been associated with ion mobility values that are within said window of ion mobility values.

The second aspect of the present invention provides a mass spectrometer for analysing a target compound or for screening for a target compound, said spectrometer comprising:

a) a chromatographic separation device for separating first ions or components of an analyte sample by retention time in the device;

b) an ion mobility separator for separating said first ions or second ions formed from said components according to ion mobility;

c) a detector;

d) one or more mass filters having a controller configured to mass filter said first ions, or mass filter second ions formed from said components, or mass filter ions derived from said first or second ions so as to transmit to said detector only ions having a mass to charge ratio corresponding to that of an ion of said target compound;

e) wherein the spectrometer is configured to detect the intensities of the ions transmitted to the detector; wherein the intensity of the ions detected at any given time is recorded together with an associated value of retention time in said chromatographic separation device and an associated value of said ion mobility so as to obtain spectral data;

f) the spectrometer further comprising a processor configured to examine the intensities of the spectral data as a function of said ion mobility so as to detect an intensity peak for said ion of said target compound in said spectral data, determine a discrete value of ion mobility for said peak, and define a window of values of ion mobility that encompasses said discrete value, wherein said window of values is narrower than the range of ion mobility values that said peak extends over; and g) a filter for filtering said spectral data so as to include only spectral data that has been associated with values of ion mobility that are within said window of ion mobility values.

The mass spectrometer may comprise:

(a) an ion source selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; (xviii) a Thermospray ion source; (xix) an Atmospheric Sampling Glow Discharge Ionisation ("ASGDI") ion source; (xx) a Glow Discharge ("GD") ion source; (xxi) an Impactor ion source; (xxii) a Direct Analysis in Real Time ("DART") ion source; (xxiii) a Laserspray Ionisation ("LSI") ion source; (xxiv) a Sonicspray Ionisation ("SSI") ion source; (xxv) a Matrix Assisted Inlet Ionisation ("MAII") ion source; (xxvi) a Solvent Assisted Inlet Ionisation ("SAII") ion source; (xxvii) a Desorption Electrospray Ionisation ("DESI") ion source; and (xxviii) a Laser Ablation Electrospray Ionisation ("LAESI") ion source; and/or (b) one or more continuous or pulsed ion sources; and/or (c) one or more ion guides; and/or (d) one or more ion mobility separation devices and/or one or more Field Asymmetric Ion Mobility Spectrometer devices; and/or (e) one or more ion traps or one or more ion trapping regions; and/or (f) one or more collision, fragmentation or reaction cells selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionisation Dissociation ("EID") fragmentation device; and/or (g) a mass analyser selected from the group consisting of: (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic mass analyser arranged to generate an electrostatic field having a quadro-logarithmic potential distribution; (x) a Fourier Transform electrostatic mass analyser; (xi) a Fourier Transform mass analyser; (xii) a Time of Flight mass analyser; (xiii) an orthogonal acceleration Time of Flight mass analyser; and (xiv) a linear acceleration Time of Flight mass analyser; and/or (h) one or more energy analysers or electrostatic energy analysers; and/or (i) one or more ion detectors; and/or (j) one or more mass filters selected from the group consisting of: (i) a quadrupole mass filter; (ii) a 2D or linear quadrupole ion trap; (iii) a Paul or 3D quadrupole ion trap; (iv) a Penning ion trap; (v) an ion trap; (vi) a magnetic sector mass filter; (vii) a Time of Flight mass filter; and (viii) a Wien filter; and/or (k) a device or ion gate for pulsing ions; and/or (l) a device for converting a substantially continuous ion beam into a pulsed ion beam.

The mass spectrometer may comprise either:

(i) a C-trap and a mass analyser comprising an outer barrel-like electrode and a coaxial inner spindle-like electrode that form an electrostatic field with a quadro-logarithmic potential distribution, wherein in a first mode of operation ions are transmitted to the C-trap and are then injected into the mass analyser and wherein in a second mode of operation ions are transmitted to the C-trap and then to a collision cell or Electron Transfer Dissociation device wherein at least some ions are fragmented into fragment ions, and wherein the fragment ions are then transmitted to the C-trap before being injected into the mass analyser; and/or (ii) a stacked ring ion guide comprising a plurality of electrodes each having an aperture through which ions are transmitted in use and wherein the spacing of the electrodes increases along the length of the ion path, and wherein the apertures in the electrodes in an upstream section of the ion guide have a first diameter and wherein the apertures in the electrodes in a downstream section of the ion guide have a second diameter which is smaller than the first diameter, and wherein opposite phases of an AC or RF voltage are applied, in use, to successive electrodes.

The mass spectrometer may comprises a device arranged and adapted to supply an AC or RF voltage to the electrodes. The AC or RF voltage optionally has an amplitude selected from the group consisting of: (i) about <50 V peak to peak; (ii) about 50-100 V peak to peak; (iii) about 100-150 V peak to peak; (iv) about 150-200 V peak to peak; (v) about 200-250 V peak to peak; (vi) about 250-300 V peak to peak; (vii) about 300-350 V peak to peak; (viii) about 350-400 V peak to peak; (ix) about 400-450 V peak to peak; (x) about 450-500 V peak to peak; and (xi) >about 500 V peak to peak.

The AC or RF voltage may have a frequency selected from the group consisting of: (i) <about 100 kHz; (ii) about 100-200 kHz; (iii) about 200-300 kHz; (iv) about 300-400 kHz; (v) about 400-500 kHz; (vi) about 0.5-1.0 MHz; (vii) about 1.0-1.5 MHz; (viii) about 1.5-2.0 MHz; (ix) about 2.0-2.5 MHz; (x) about 2.5-3.0 MHz; (xi) about 3.0-3.5 MHz; (xii) about 3.5-4.0 MHz; (xiii) about 4.0-4.5 MHz; (xiv) about 4.5-5.0 MHz; (xv) about 5.0-5.5 MHz; (xvi) about 5.5-6.0 MHz; (xvii) about 6.0-6.5 MHz; (xviii) about 6.5-7.0 MHz; (xix) about 7.0-7.5 MHz; (xx) about 7.5-8.0 MHz; (xxi) about 8.0-8.5 MHz; (xxii) about 8.5-9.0 MHz; (xxiii) about 9.0-9.5 MHz; (xxiv) about 9.5-10.0 MHz; and (xxv) >about 10.0 MHz.

The mass spectrometer may comprise a chromatography or other separation device upstream of an ion source. The chromatography separation device may comprise a liquid chromatography or gas chromatography device. The separation device may comprise: (i) a Capillary Electrophoresis ("CE") separation device; (ii) a Capillary Electrochromatography ("CEC") separation device; (iii) a substantially rigid ceramic-based multilayer microfluidic substrate ("ceramic tile") separation device; or (iv) a supercritical fluid chromatography separation device.

The ion guide may be maintained at a pressure selected from the group consisting of: (i) <about 0.0001 mbar; (ii) about 0.0001-0.001 mbar; (iii) about 0.001-0.01 mbar; (iv) about 0.01-0.1 mbar; (v) about 0.1-1 mbar; (vi) about 1-10 mbar; (vii) about 10-100 mbar; (viii) about 100-1000 mbar; and (ix) >about 1000 mbar.

Analyte ions may be subjected to Electron Transfer Dissociation ("ETD") fragmentation in an Electron Transfer Dissociation fragmentation device. Analyte ions may be caused to interact with ETD reagent ions within an ion guide or fragmentation device.

In order to effect Electron Transfer Dissociation, optionally either: (a) analyte ions are fragmented or are induced to dissociate and form product or fragment ions upon interacting with reagent ions; and/or (b) electrons are transferred from one or more reagent anions or negatively charged ions to one or more multiply charged analyte cations or positively charged ions whereupon at least some of the multiply charged analyte cations or positively charged ions are induced to dissociate and form product or fragment ions; and/or (c) analyte ions are fragmented or are induced to dissociate and form product or fragment ions upon interacting with neutral reagent gas molecules or atoms or a non-ionic reagent gas; and/or (d) electrons are transferred from one or more neutral, non-ionic or uncharged basic gases or vapours to one or more multiply charged analyte cations or positively charged ions whereupon at least some of the multiply charged analyte cations or positively charged ions are induced to dissociate and form product or fragment ions; and/or (e) electrons are transferred from one or more neutral, non-ionic or uncharged superbase reagent gases or vapours to one or more multiply charged analyte cations or positively charged ions whereupon at least some of the multiply charge analyte cations or positively charged ions are induced to dissociate and form product or fragment ions; and/or (f) electrons are transferred from one or more neutral, non-ionic or uncharged alkali metal gases or vapours to one or more multiply charged analyte cations or positively charged ions whereupon at least some of the multiply charged analyte cations or positively charged ions are induced to dissociate and form product or fragment ions; and/or (g) electrons are transferred from one or more neutral, non-ionic or uncharged gases, vapours or atoms to one or more multiply charged analyte cations or positively charged ions whereupon at least some of the multiply charged analyte cations or positively charged ions are induced to dissociate and form product or fragment ions, wherein the one or more neutral, non-ionic or uncharged gases, vapours or atoms are selected from the group consisting of: (i) sodium vapour or atoms; (ii) lithium vapour or atoms; (iii) potassium vapour or atoms; (iv) rubidium vapour or atoms; (v) caesium vapour or atoms; (vi) francium vapour or atoms; (vii) $C_{60}$ vapour or atoms; and (viii) magnesium vapour or atoms.

The multiply charged analyte cations or positively charged ions may comprise peptides, polypeptides, proteins or biomolecules.

In order to effect Electron Transfer Dissociation, optionally: (a) the reagent anions or negatively charged ions are derived from a polyaromatic hydrocarbon or a substituted polyaromatic hydrocarbon; and/or (b) the reagent anions or negatively charged ions are derived from the group consisting of: (i) anthracene; (ii) 9,10 diphenyl-anthracene; (iii) naphthalene; (iv) fluorine; (v) phenanthrene; (vi) pyrene; (vii) fluoranthene; (viii) chrysene; (ix) triphenylene; (x) perylene; (xi) acridine; (xii) 2,2' dipyridyl; (xiii) 2,2' biquinoline; (xiv) 9-anthracenecarbonitrile; (xv) dibenzothiophene; (xvi) 1,10'-phenanthroline; (xvii) 9' anthracenecarbonitrile; and (xviii) anthraquinone; and/or (c) the reagent ions or negatively charged ions comprise azobenzene anions or azobenzene radical anions.

The process of Electron Transfer Dissociation fragmentation may comprise interacting analyte ions with reagent ions, wherein the reagent ions comprise dicyanobenzene, 4-nitrotoluene or azulene.

A chromatography detector may be provided wherein the chromatography detector comprises either: a destructive chromatography detector optionally selected from the group consisting of (i) a Flame Ionization Detector (FID); (ii) an aerosol-based detector or Nano Quantity Analyte Detector (NQAD); (iii) a Flame Photometric Detector (FPD); (iv) an Atomic-Emission Detector (AED); (v) a Nitrogen Phosphorus Detector (NPD); and (vi) an Evaporative Light Scattering Detector (ELSD); or a non-destructive chromatography detector optionally selected from the group consisting of: (i) a fixed or variable wavelength UV detector; (ii) a Thermal Conductivity Detector (TCD); (iii) a fluorescence detector; (iv) an Electron Capture Detector (ECD); (v) a conductivity monitor; (vi) a Photoionization Detector (PID); (vii) a Refractive Index Detector (RID); (viii) a radio flow detector; and (ix) a chiral detector.

The mass spectrometer may be operated in various modes of operation including a mass spectrometry ("MS") mode of operation, a tandem mass spectrometry ("MS/MS") mode of operation, a mode of operation in which parent or precursor ions are alternatively fragmented or reacted so as to produce fragment or product ions, and not fragmented or reacted or fragmented or reacted to a lesser degree, a Multiple Reaction Monitoring ("MRM") mode of operation, a Data Dependent Analysis ("DDA") mode of operation, a Data Independent Analysis ("DIA") mode of operation, a Quantification mode of operation or an Ion Mobility Spectrometry ("IMS") mode of operation.

The method disclosed herein may provide high precision peak detected mobility data to generate a chromatogram. This may be used in combination with single or tandem mass filters and reduces the likelihood of false positives in targeted analysis. The technique can also lead to improved signal to noise and hence improved detection limits.

The spectrometer may comprise an ion mobility separator (IMS) coupled to one or more mass filter. The ions transmitted by the mass filter are separated according to their ion mobility in the IMS device during each dwell time. The ions are detected at a detector. The current at the detector is monitored as ions elute from the IMS device and an IMS spectrum is recorded during each dwell time.

The ion mobility separator may be upstream or downstream of the mass to charge ratio filter or filters.

The mobility spectra may be processed or peak detected to produce a single drift time value for each detected mobility peak at each dwell time, with high statistical precision, reproducibility and (assuming good initial mobility calibration) high accuracy.

Reconstructed 'exact' mobility chromatograms may be generated from the processed or centroided mobility spectra using drift time windows less than the width of the mobility peaks and centred on known or expected drift time of the analyte from prior calibration.

This invention may add a degree of specificity beyond the absolute resolution of the IMS peaks to help exclude matrix signals which may be within the expected retention window of the analyte and are chromatographically resolved. This can reduce false positives and improve chromatographic signal to noise.

In addition, the standard deviation of non-chromatographic baseline noise may also be decreased by using a narrow drift time window around the centroid value as the signal from target ions necessarily has higher precision than the less intense background signal and therefore is more consistently within the narrow drift time window.

Unlike chromatographic retention time, IMS drift time is reproducible and robust for a given set of conditions. Using standards, the IMS drift time values for each target analyte may be determined prior to analysis of the analyte mixture. Alternatively the IMS may be calibrated and collision cross-section (CCS) values calculated for the analytes to further improve robustness.

BRIEF DESCRIPTION OF THE DRAWINGS

Various embodiments of the present invention will now be described, by way of example only, and with reference to the accompanying drawings in which.

DETAILED DESCRIPTION

Figure 1:
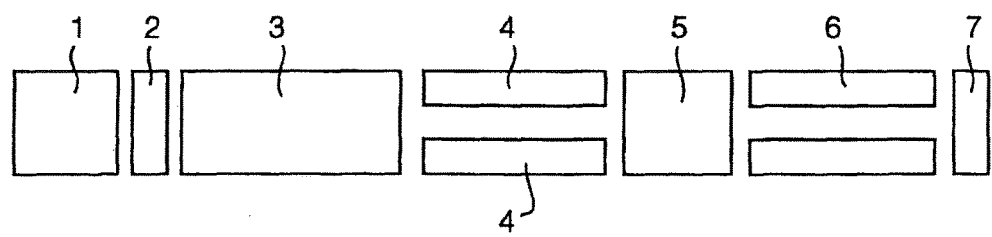
FIG. 1 shows a schematic of a spectrometer according to the present invention.

FIG. 1 shows a schematic of an ion mobility separation (IMS) tandem quadrupole instrument according to an embodiment of the present invention. The instrument comprises an ion source 1, an ion trap 2, an IMS device 3, a first quadrupole mass filter 4, a fragmentation or reaction device 5 for fragmenting or reacting ions, a second quadrupole mass filter 6 and a detector 7.

In operation, ions are produced by ion source 1 and are then accumulated in ion trap 2. The ion trap 2 periodically releases or pulses the ions into IMS device 3. The ions separate according to their ion mobilities through the gas in the IMS device 3 as they pass through the IMS device 3. Ions therefore elute from the IMS device 3 in order of their ion mobility and then enter quadrupole mass filter 4. Quadrupole mass filter 4 is set so as to transmit only a range of mass to charge ratios of interest during at least part of the time that ions elute from the IMS device 3. Other ions are filtered out by the mass filter 4. Ions which have been transmitted by the mass filter 4 may be dissociated or reacted in fragmentation or reaction device 5 so as to form fragment or product ions. The resulting fragment or product ions are then transmitted to mass filter 6. This mass filter 6 is set so as to transmit only ions having a second mass to charge ratio or range of mass to charge ratios that correspond to a characteristic fragment or product ion. Other ions are filtered out by mass filter 6. The ions that are transmitted by the mass filter 6 are then detected by detector 7.

Figure 2:
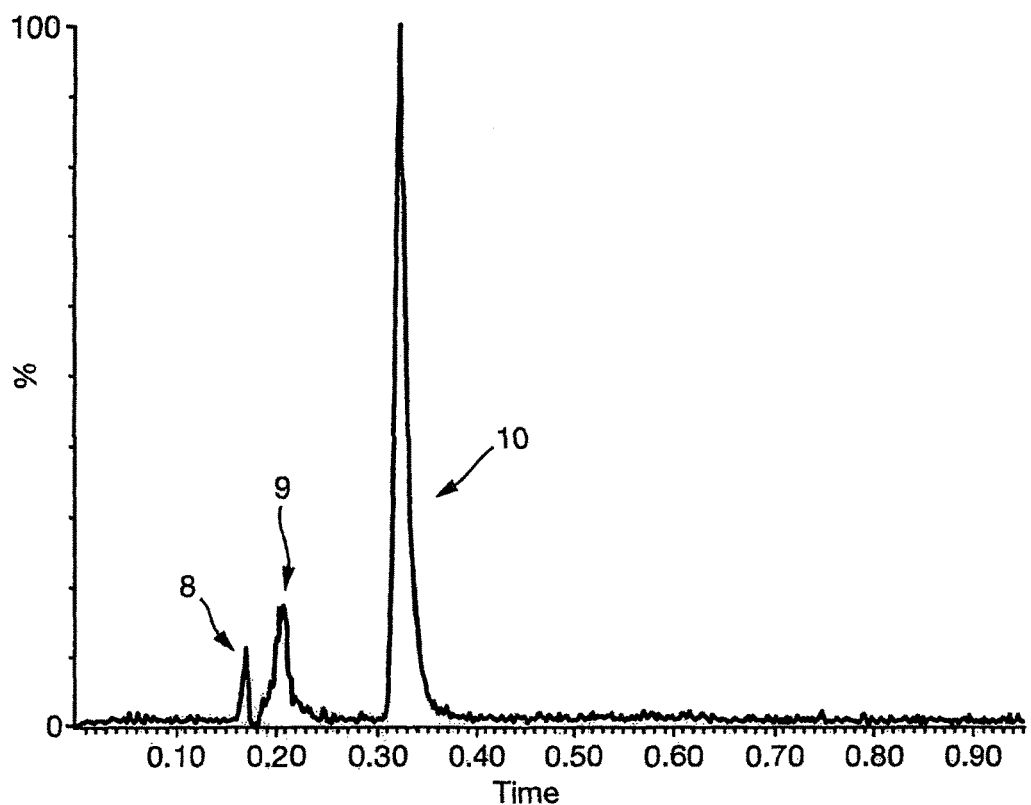
FIG. 2 shows an ion chromatogram spectrum produced using the instrument of FIG. 1 and shows an analyte peak and two contaminant peaks.

FIG. 2 is an ion chromatogram showing the total ion current as a function of liquid chromatography retention time for an elution of Acetaminophen 1 pg on column using the instrument of FIG. 1. The chromatography column was an Acquity BEH C18 1.7 μm 2.1×50 mm column. The mobile phase comprised: A) water +0.1% formic acid; and B) Acetonitrile+0.1% formic acid. The gradient was 0 to 1.8 mins 10% to 90% B at 0.65 mL/min.

The multiple reaction monitoring (MRM) transition quadrupole mass filter 4 (Q1) was set to transmit ions having a mass to charge ratio of 152.1. The second mass filter 6 (Q2) was set to transmit ions having a mass to charge ratio of 110.1. Both mass filters 4,6 were set to transmit ions with a mass to charge ratio window of approximately +/−0.5 amu. Ions were directed into the fragmentation or reaction device 5 with a collision energy of 14 eV.

Each pulse of ions was ejected from the ion trap 2 into the IMS device 3 with a gate time of 150 μs. The dwell time between consecutive pulses of ions being transmitted from the ion trap 2 into the IMS device 3 was set to 15 ms. Ions pulsed into the IMS device 3 separated according to their ion mobilities within the IMS device 3 during this dwell time. During this period, further ions were prevented from entering the IMS device 3 and were accumulated in the ion trap 2. An inter-channel delay time of 3 ms was provided.

The acquisition system was set to record the signal arriving at the detector 7 at regular time intervals during the IMS separation time. This resulted in an IMS spectrum from precursor ions having a mass to charge ratio of 152.1+/−0.5 amu, which gave rise to fragment or product ions having a mass to charge ratio of 110.1+/−0.5 amu being recorded at each dwell time period. The spectrum shown in FIG. 2 therefore represents ions having a mass to charge ratio of 110.1+/−0.5 amu that are transmitted by the second mass filter 6.

FIG. 2 shows that three peaks 8, 9, 10 are present in the total ion current (TIC) for this MRM transition. There is also significant baseline noise present below each peak. Peak 10 is from Acetaminophen, whereas peaks 8 and 9 are both background peaks from contaminants within the solvent or sample. Although peaks 8, 9 and 10 are well resolved by LC retention time it will be appreciated that this will not be the case for all compounds and it is therefore desired to provide an improved method of resolving compounds.

During this experiment several other MRM transitions were also recorded in a sequential, cyclic manner by changing the mass to charge ratios transmitted by the quadrupole mass filter 4 and/or mass filter 6 during the inter-channel delay time. Although these data were acquired, they are not shown for simplicity.

For each sample point in FIG. 2 the ion current for ions transmitted by the second mass filter 6 is detected and recorded along with its associated LC retention time, i.e. the retention time of the compound that gave rise to the detected ion is recorded along with the ion signal. For example, each analyte elutes from the LC device at a particular retention time, may be fragmented in the collision cell 5 and is then be detected at detector 7. At each data sampling point, the ion signal for each fragment ion is recorded along with the LC retention time of its respective precursor analyte ion and used to form a data point in FIG. 2.

For each sample point in FIG. 2, in addition to recording the LC retention time associated with the detected ions, the associated drift time through the IMS device 3 is also recorded. In other words, the drift time of the ion that gave rise to the detected ion is recorded along with the ion signal. For example, each precursor ion passes through the IMS device with a particular drift time, may be fragmented in the collision cell 5 and is then be detected at detector 7. At each data sampling point, the ion signal for each fragment ion is recorded along with the drift time of its respective precursor analyte ion. This data is used to form IMS spectra, as will be described with reference to FIGS. 3A-3C.

Figure 3A:
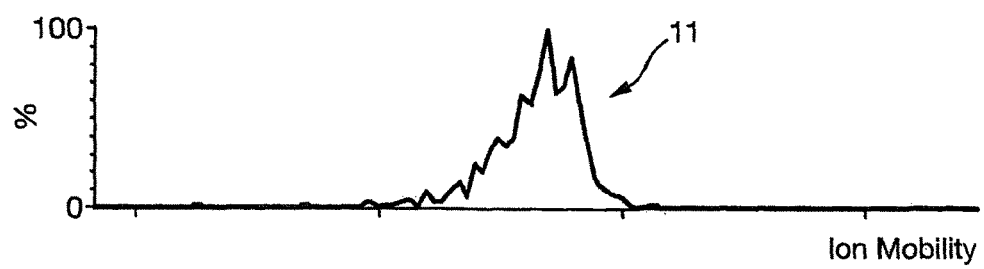
FIGS. 3A-3C show ion mobility spectra related to the analyte and contaminants of FIG. 2.
Figure 3B:
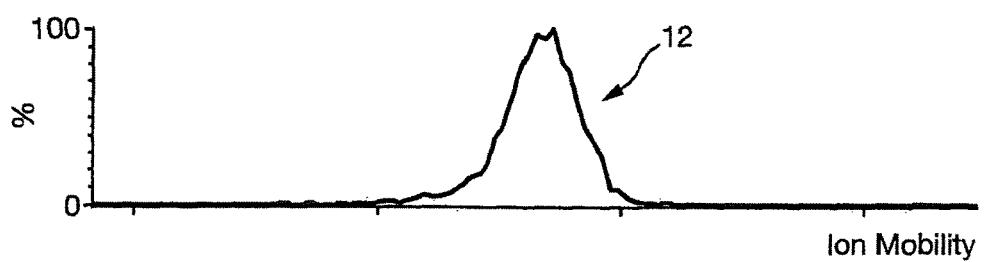
Figure 3C:
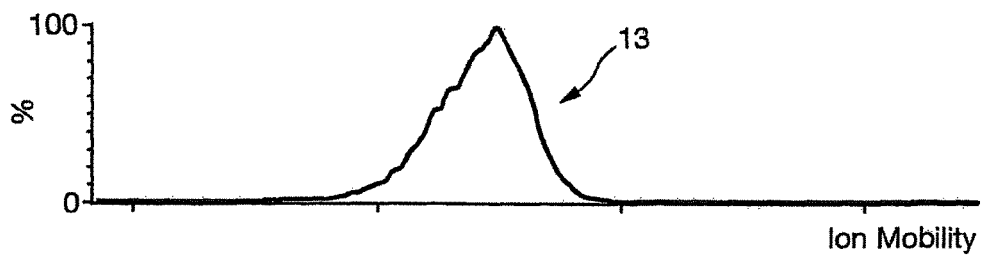

FIGS. 3A-3C show IMS spectra for the peaks in FIG. 2. The increasing values of the x-axis represent decreasing drift time values through the IMS device 3, i.e. increasing ion mobilities. Peak 11 in FIG. 3A represents the portion of the spectra of FIG. 2 for peak 8. Peak 12 in FIG. 3B represents the portion of the spectra of FIG. 2 for peak 9. Peak 13 in FIG. 3C represents the portion of the spectra of FIG. 2 for peak 10. It can be seen from FIGS. 3A-3C that the drift time for both background ion peaks 11,12 is lower than the drift time for the Acetaminophen peak 13 and that the IMS drift time may be used to help resolve peaks.

Figure 4A:
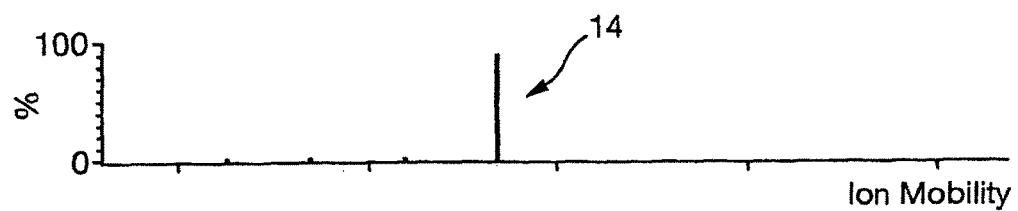
FIGS. 4A-4C show the same data as FIGS. 3A-3C, respectively, except after peak detection of the spectra.
Figure 4B:
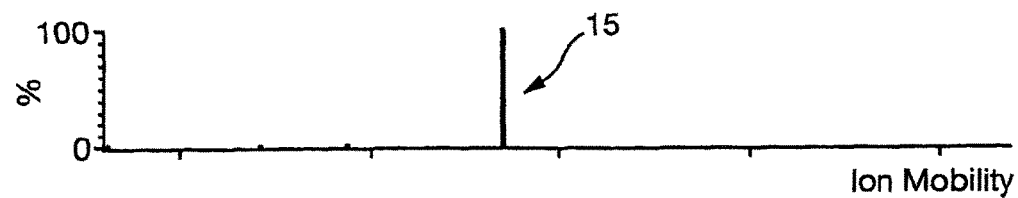
Figure 4C:
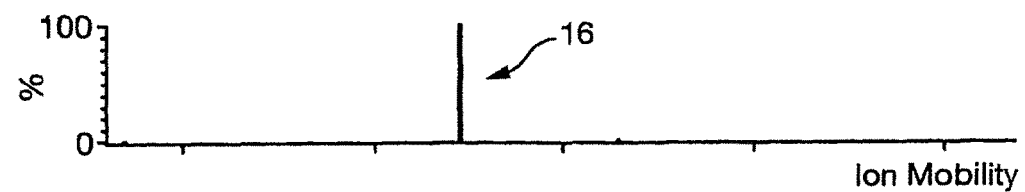

FIGS. 4A-4C show the same data as FIGS. 3A-3C, respectively, except after peak detection of the IMS spectra. Each individual IMS spectra for each dwell time is separately peak detected to determine the centroid value and area of each IMS peak. This resulted in a separate centroided data file in which each peak in each IMS spectrum was reduced to IMS drift time and intensity pairs. Peaks 14, 15 and 16 in FIGS. 4A-4C correspond to the centroid values of peaks 11, 12 and 13 respectively in FIGS. 3A-3C. Peak 16 represents Acetaminophen. The method described herein may be a method of targeted spectrometry, wherein the ion mobility of the target analyte is accurately determined or known before the experimental run. The centroided peak of the target analyte, Acetaminophen, in FIG. 4C may then be calibrated using the predetermined or known accurate value of its ion mobility.

As Acetaminophen is the compound of interest, peak 15 is selected and a window of ion mobility values about peak 15 is defined. The window of ion mobility values may be selected so as not to encompass the ion mobilities of the other peaks, i.e. peaks 14 and 15. The mass spectral data obtained using the instrument of FIG. 1 is then filtered so as to only include data having ion mobilities in the window of ion mobilities. The total ion current can then be plotted as a function of LC retention time for this remaining data. This filtered data is represented in FIG. 5.

Figure 5:
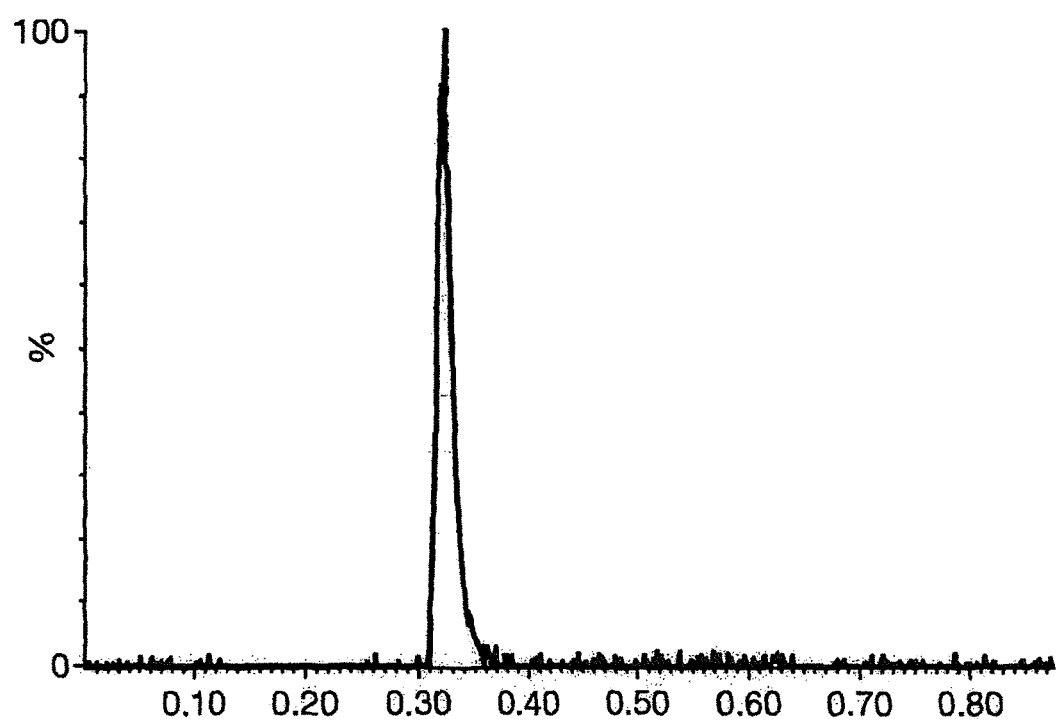
FIG. 5 shows the reconstructed chromatogram of FIG. 2 after data relating to the contaminants has been excluded.

FIG. 5 shows the same data as in FIG. 2, except filtered so as to include only data associated with an IMS drift time that is within the drift time window about peak 16 in FIG. 4C, i.e. within the window about the peak for Acetaminophen. It can be seen that both of the background ion signals (i.e. peaks 8 and 9 in FIG. 2) have been successfully excluded from the final chromatogram on the basis of their IMS drift time, leaving only signal from the target analyte, Acetaminophen. In addition, the general baseline noise has been reduced, leading to improved detection limits.

It will be appreciated that the use of high precision peak detected mobility data to generate chromatograms such as that shown in FIG. 5 reduces the likelihood of false positives and can lead to improved signal to noise and hence improved detection limits. The IMS drift time filtered chromatogram may be used for quantification after calibration with standards.

The data processing described may be performed in real time over the entire drift time range. Alternatively, the data processing may be performed over only a specified narrow region or regions of drift time in which the target peaks are expected to appear for a given retention time range. This reduces the amount of data saved to disk and reduces the computational overhead.

Processed data for each dwell time may include intensity and drift time. Other meta data extracted during processing may be included such as, for example, peak width, skew, kurtosis, height or other measures of IMS peak shape. This information may be used during post processing.

Although the present invention has been described with reference to various embodiments, it will be understood by those skilled in the art that various changes in form and detail may be made without departing from the scope of the invention as set forth in the accompanying claims.

For example, although the IMS device has been described as being prior to the mass filter the IMS device may be downstream of one or both of the mass filters without deviating from the invention.

As described in relation to FIGS. 4A-4C, the method comprises determining a precise drift time for each peak. Many methods of determining precise drift time are known and may be used. For example, peak top fitting using polynomials or fitting model peak shapes, probabilistic or Bayesian methods may be employed. Deconvolution methods such as the clean algorithm or non-negative least squares may be used.

The drift time measurement may be converted to interaction cross-section or collision cross-section (CCS) by using a suitable calibration technique and then reconstructed accurate CCS chromatograms may be generated.

Measures of peak purity or peak shape such as skew, kurtosis or deviations from model peak shapes may be recorded during peak detection of the ion mobility data. Reconstructed chromatograms may be generated based on minimum peak purity criteria, effectively excluding signals with potential IMS interference which appear within the drift time widow selected. Alternatively these signals may be flagged as suspect or corrupt.

The continuum or profile IMS data may be processed as a full two dimensional, retention time, drift time (RT, DT) data set using a 2D peak detection or deconvolution algorithm. This produces a list of (RT, DT, intensity) points for each RT-DT peak. This list may be filtered in the same way as described above using a drift time window that is narrower than the width of the IMS peak so as to remove false positives.

The width of the drift time or CCS windows used may be automatically calculated from the calculated statistical precision of each accurate drift time or CCS measurement based on the width of the IMS peak and the number of ion events present.

A lock drift channel may be used to ensure accurate IMS measurements. In this mode an internal or external standard of known CCS or known drift time is periodically monitored and the CCS or drift time of the analyte peak is corrected for any drift based on the measurement of drift time for the standard.

The invention claimed is:

1. A method of mass spectrometry comprising:
   a) separating first ions or components of an analyte sample according to a physicochemical property other than ion mobility;
   b) separating said first ions or second ions formed from said components according to ion mobility;
   c) detecting the intensities of said first ions, or detecting the intensities of second ions formed from said components, or detecting the intensities of ions derived from said first or second ions; wherein the intensity of the ions detected at any given time is recorded together with an associated value of said physicochemical property and an associated value of said ion mobility so as to obtain spectral data;
   d) examining the intensities of the spectral data as a function of said ion mobility so as to detect an intensity peak in said spectral data, determining a discrete value of ion mobility for said peak, and defining a window of values of ion mobility that encompasses said discrete value; and
   e) filtering said spectral data so as to include only spectral data that has been associated with values of ion mobility that are within said window of ion mobility values.

2. The method of claim 1, comprising examining the intensities of the filtered spectral data as a function of said physicochemical property so as to detect an intensity peak in said filtered spectral data, and optionally identifying the presence or quantity of a compound in the sample being analysed from the intensity peak of the filtered spectral data.

3. The method of claim 2, wherein said method is a method of targeted mass spectrometry for analysing a target compound, or wherein said method is a method of screening a sample for a target compound; wherein the intensity peak detected in step d) and/or the intensity peak detected in claim 2 is the intensity peak for an ion of said target compound.

4. The method of claim 3, comprising mass filtering the ions so as to transmit only ions of a single mass to charge ratio or a range of mass to charge ratios to a detector that performs said step of detecting, wherein said single mass to charge ratio or range of mass to charge ratios includes the mass to charge ratio of said ion of said target compound.

5. The method of claim 1, wherein the physicochemical property is the elution time from a separation device, optionally from a chromatographic separation device.

6. The method of claim 1, comprising fragmenting, reacting or activating said first ions of step a) or said second ions of step b) so as to form said ions derived from said first or second ions in step c).

7. The method of claim 6, comprising mass filtering said first ions or said second ions so that only ions of a single mass to charge ratio or a predetermined range of mass to charge ratios are subjected to said fragmenting, reacting or activating; and/or
   mass filtering said ions derived from said first or second ions so that only ions of a single mass to charge ratio or a predetermined range of mass to charge ratios are detected.

8. The method of claim 1, wherein the associated value of said physicochemical property for the ions detected at any given time in step c) is based on the time at which said the ions are detected; and/or wherein the associated value of said ion mobility for the ions detected at any given time in step c) is based on the time at which the ions are detected.

9. The method of claim 1, comprising the step of separating the first ions or separating the components of the analyte sample according to said physicochemical property; and then
   separating said first ions or second ions according to said ion mobility; and then
   fragmenting, reacting or activating the first or second ions so as to form said ions derived from said first or second ions; and then
   detecting the intensities of said ions derived from said first or second ions;
   wherein the intensity of the ions detected at any given time is recorded together with an associated value of said physicochemical property and an associated value of said ion mobility so as to obtain said spectral data;

wherein the value of said physicochemical property that is associated with the ions detected at any given time is determined based on the time that the ions are detected; and wherein the value of the ion mobility that is associated with the ions detected at any given time is determined based on the time that the ions are detected.

10. The method of claim 9, wherein said physicochemical property is the retention time in a separation device, and wherein the value of said physicochemical property that is associated with the ions detected at any given time is the retention time of the ions in said first ions from which said detected ions are derived, or is the retention time of the component in said components of an analyte sample from which said detected ions are derived; and/or wherein the value of said ion mobility that is associated with the ions detected at any given time is the ion mobility of the ions in said first ions from which said detected ions are derived.

11. The method of claim 1, wherein the discrete value determined in step d) is obtained by determining a centroid of the intensity peak in step d).

12. The method of claim 1, wherein said window of values for said ion mobility is narrower than the range of ion mobility values that the peak in step d) extends over.

13. The method of claim 1, wherein the intensities of the spectral data as a function of said ion mobility includes a plurality of intensity peaks, each peak spanning over a different range of ion mobility values, wherein said window of values is determined for one of said peaks, and wherein the width of said window is selected to be narrow enough so as to exclude at least some of the values of ion mobility that are in one or more other peaks.

14. The method of claim 13, comprising determining a discrete value of ion mobility for each of said one or more other peaks, and wherein said window is defined so as to exclude the discrete value(s) of said one or more other peaks.

15. A method of mass spectrometry for analysing a target compound or for screening for a target compound, said method comprising:
   a) separating first ions or components of an analyte sample by retention time in a chromatographic separation device;
   b) separating said first ions or second ions formed from said components according to ion mobility in an ion mobility separator;
   c) mass filtering said first ions, or mass filtering second ions formed from said components, or mass filtering ions derived from said first or second ions so as to transmit to a detector only ions having a mass to charge ratio corresponding to that of an ion of said target compound;
   d) detecting the intensities of the ions transmitted to the detector; wherein the intensity of the ions detected at any given time is recorded together with an associated value of retention time in said chromatographic separation device and an associated value of said ion mobility so as to obtain spectral data;
   e) examining the intensities of the spectral data as a function of said ion mobility so as to detect an intensity peak for said ion of said target compound in said spectral data, determining a discrete value of ion mobility for said peak, and defining a window of values of ion mobility that encompasses said discrete value, wherein said window of values is narrower than the range of ion mobility values that said peak extends over; and
   f) filtering said spectral data so as to include only spectral data that has been associated with values of ion mobility that are within said window of ion mobility values.

16. A mass spectrometer arranged and configured to perform the method of claim 1.

17. A mass spectrometer comprising:
   a) a separator for separating first ions or components of an analyte sample according to a physicochemical property other than ion mobility;
   b) an ion mobility separator for separating said first ions or second ions formed from said components according to ion mobility;
   c) a detector for detecting the intensities of said first ions, or detecting the intensities of second ions formed from said components, or detecting the intensities of ions derived from said first or second ions; wherein the spectrometer is configured such that the intensity of the ions detected at any given time is recorded together with an associated value of said physicochemical property and an associated value of said ion mobility so as to obtain spectral data; and
   d) a processor for examining the intensities of the spectral data as a function of said ion mobility so as to detect an intensity peak in said spectral data, determine a discrete value of said ion mobility for said peak, and set a window of values for said ion mobility that encompasses said discrete value; and for filtering said spectral data so as to include only spectral data that has been associated with ion mobility values that are within said window of ion mobility values.

18. A mass spectrometer for analysing a target compound or for screening for a target compound, said spectrometer comprising:
   a) a chromatographic separation device for separating first ions or components of an analyte sample by retention time in the device;
   b) an ion mobility separator for separating said first ions or second ions formed from said components according to ion mobility;
   c) a detector;
   d) one or more mass filters having a controller configured to mass filter said first ions, or mass filter second ions formed from said components, or mass filter ions derived from said first or second ions so as to transmit to said detector only ions having a mass to charge ratio corresponding to that of an ion of said target compound;
   e) wherein the spectrometer is configured to detect the intensities of the ions transmitted to the detector; wherein the intensity of the ions detected at any given time is recorded together with an associated value of retention time in said chromatographic separation device and an associated value of said ion mobility so as to obtain spectral data;
   f) the spectrometer further comprising a processor configured to examine the intensities of the spectral data as a function of said ion mobility so as to detect an intensity peak for said ion of said target compound in said spectral data, determine a discrete value of ion mobility for said peak, and define a window of values of ion mobility that encompasses said discrete value, wherein said window of values is narrower than the range of ion mobility values that said peak extends over; and g) a filter for filtering said spectral data so as to include only spectral data that has been associated with values of ion mobility that are within said window of ion mobility values.

\* \* \* \* \*